(12) United States Patent
Suh et al.

(10) Patent No.: US 6,428,801 B1
(45) Date of Patent: Aug. 6, 2002

(54) METHODS FOR CONTROLLING DUST MITES AND THE ALLERGENS PRODUCED BY DUST MITES

(75) Inventors: Janette Suh, New Milford; Laura Vaccaro, Montclair; Robert Bogart, River Vale, all of NJ (US)

(73) Assignee: Reckitt Benckiser Inc., Wayne, NJ (US)

( * ) Notice: Subject to any disclaimer, the term of this patent is extended or adjusted under 35 U.S.C. 154(b) by 0 days.

(21) Appl. No.: 09/583,612

(22) Filed: May 31, 2000

(30) Foreign Application Priority Data

Aug. 6, 1997 (GB) .............................................. 9716539

(51) Int. Cl.[7] .............................................. A01N 25/06
(52) U.S. Cl. ........................... 424/407; 424/43; 424/45; 424/403; 424/404; 424/405; 424/406; 514/544
(58) Field of Search ........................... 424/43, 45, 403, 424/404, 405, 406, 407, 78.08; 514/724, 544

(56) References Cited

U.S. PATENT DOCUMENTS

| 4,048,369 A | 9/1977 | Johnson ...................... 428/262 |
| 4,666,940 A | 5/1987 | Bischoff et al. ............. 514/544 |
| 4,800,196 A | 1/1989 | Nomura et al. .............. 514/159 |
| 4,806,526 A | 2/1989 | Green .......................... 514/23 |
| 5,180,586 A | 1/1993 | Sato et al. ................... 424/405 |
| 5,204,090 A | 4/1993 | Han .............................. 424/59 |
| 5,271,947 A | 12/1993 | Miller et al. ................. 424/680 |
| 5,508,024 A | 4/1996 | Tranner ........................ 424/59 |
| 5,620,683 A | 4/1997 | Tong et al. ............... 424/70.11 |
| 5,686,062 A | 11/1997 | Tong ............................ 424/47 |
| 5,695,677 A | 12/1997 | Silvester et al. ........... 252/8.91 |
| 5,830,440 A | 11/1998 | Sturla et al. .................. 424/47 |

FOREIGN PATENT DOCUMENTS

| AU | B-69067/87 | 8/1987 | .......... A01N/53/00 |
| CH | 563777 | * 7/1975 | |
| DE | 39 41 572 A | 6/1991 | ............ A61K/7/00 |
| EP | 0612469 A1 | 8/1994 | .......... A01N/25/00 |
| GB | 1368657 | 10/1974 | ............ A01N/9/24 |
| GB | 2058819 | 9/1979 | ............ C09K/3/30 |
| GB | 1572224 | 7/1980 | ............ C09K/3/30 |
| GB | 1578331 | 11/1980 | ............ C09K/3/30 |
| GB | 1582617 | 1/1981 | ............ C09K/3/30 |
| GB | 2058820 | 4/1981 | ............ C09K/3/30 |
| GB | 1595649 | 8/1981 | ............ C09K/3/30 |
| GB | 1602420 | 11/1981 | ......... C08F/226/00 |
| GB | 2042893 | 1/1990 | .......... A01N/25/02 |
| GB | 2300122 A | 10/1996 | .......... A01N/25/00 |
| JP | 60142906 | * 12/1983 | |
| WO | WO89/12673 | 12/1989 | ............ C11D/3/48 |
| WO | WO96/00564 A | 1/1996 | ............ A61K/7/09 |

OTHER PUBLICATIONS

Control of House–Dust Mites (Pyroglyphidae) with Home Disinfectants, Schober et al., Experimental & Applied Acarology, 3 (1987) pp. 179–189.
The Journal of Indoor Air International Indoor Environment, Jul.–Aug. 1992, pp. 212–218.
Derwent Abstract: JP 5–265604–A.
Derwent Abstract: JP 60–142906–A.
Abstract: Hart et al. "In Vitro Evaluation of Acaricidal and Fungicidal Activity . . . ", Clin. Exp. Allergy 22:923–28 (1992).
Abstract: JP 1–100101–A.
Abstract: Ottoboni et al., "House Dust Mites Prevention in Italy", Bol. di Zoologica Agracia et di Barchicoltura 24:113–120 (1992).
Abstract: JP 3–77820–A.
PCT International Search Report for PCT Application No. PCT/GB98/02253 dated Nov. 26, 1998.
Copy of GB Patent Office Search Report for GB 9716539.3 dated Oct. 7, 1997.
Derwent Publication Abstract No. JP 60–42314–A.
Derwent Publication Abstract No. JP 61–91103–A.
Derwent Publication Abstract No. JP 3–31206–A.

* cited by examiner

*Primary Examiner*—Neil S. Levy
(74) *Attorney, Agent, or Firm*—Fish & Richardson P.C.

(57) ABSTRACT

Alcohol based aerosol spray compositions which contain 1–20% of an alcohol-soluble polymer which, on evaporation, leaves on a sprayed surface a film which acts as a barrier to dust, dust mites and their faecal excretions. These compositions optionally can include an acaricidal ingredient, such as benzyl benzoate, and one or more antimicrobial ingredients such as a quaternary ammonium salt.

18 Claims, No Drawings

METHODS FOR CONTROLLING DUST MITES AND THE ALLERGENS PRODUCED BY DUST MITES

FIELD OF THE INVENTION

This invention relates to alcohol-based disinfectant compositions containing one or more additional ingredients which form a barrier against dust particles and particularly dust mites and their allergens. More specifically, the invention relates to aerosol spray disinfectants suitable for indoor use which, in addition to having the usual antimicrobial properties, are also effective in preventing people from coming in contact with allergens found in dust, notably dust mite allergens. The invention also provides methods for effectively controlling dust mites and their allergens and for significantly reducing their attendant adverse reactions.

BACKGROUND OF THE INVENTION

Common house dust is an important cause of asthma, rhinitis, atopic dermatitis, eczema and other allergic conditions in sensitive individuals. Household dust generally comprises a variety of particulate matter including pollen, dust mites, dust mite allergens, dirt, skin cells, animal dander, insect parts, pillow feathers, food particles and mould spores. The particular constituents of dust will depend on location within the house, whether pets are present and other obvious factors. One of the principal sources of allergies is dust mites, which inhabit rugs, carpets, and other fabric surfaces, particularly sofas, mattresses, pillows, upholstered chairs and the like. The mite *Dermatophygoides pteronyssinus* has been identified as a major source of house dust allergen. This mite and the related mites *D. farinae, D. microceras* and *Euroglyphus maynei* are the predominant house dust mites in temperate climates in North America, Europe, Australia and other areas.

Dust mites are not insects, but are eight-legged arachnids, relatives to ticks and spiders. They live in close association with humans (or other mammals), their main food source being the shed scales from skin. Adult mites are approximately 300 microns (3/10 mm) in size, having developed over approximately 25 days through egg, larval and nymph stages. Adults live for 2 to 3½ months, during which time each female can produce about 20–40 eggs. Dust mites are photophobic, living deep in pillows, mattresses, carpets, upholstered furniture and other soft materials.

In addition to a food source, the other essential requirement for dust mite growth is adequate humidity. Dust mites are 75% water by weight. They do not drink water, but must absorb water vapor from the air in order to survive. Specialized glands above their pairs of legs produce secretions high in sodium and potassium chloride, which act to absorb water vapor from surrounding air. This can only be accomplished if the surrounding humidity is sufficiently high. Relative humidities of about 65–80% at temperatures ranging from about 20 to 35 C are optimal for dust mite growth. Dust mites will die at humidities of 50% or less. In geographical areas where humidity is high, dust mites are present in nearly all homes and may be as plentiful as 18,000 mites per gram of dust. Literally millions of mites can inhibit a single bed or rug.

A major dust mite allergen is present in mite faecal particles. Each mite produces about 20 faecal particles per day, and more than 100,000 of them may be present in a gram of dust. These particles vary from about 10 to 40 microns in size, comparable to the size of pollen grains, and become airborne during domestic activity such as making beds and vacuuming carpets.

Group I allergens (dermatophagoides farinae I-Der f I and dermatophagoides pteronyssinus I-Der p I) are heat labile, 24,000 molecular weight glycoproteins (hydrolytic enzymes). These allergens appear to be structural homologues and have very similar N-terminal amino acid sequences. These group I allergens are regarded as the most important and are excreted in their highest concentrations by the mite's gastrointestinal tract in the form of mite's faecal particles, suggesting that they are associated with digestion. They elute rapidly (within 2 minutes) from isolated faecal particles, but very slow from mite bodies.

Group II allergens (Der p II and Der f II) are 15,000 molecular weight proteins with almost identical N-terminal amino acid sequences that are also secreted by the mite's gastrointestinal tract in the form of faecal allergens, although not in as high a concentration as the group I allergens. This suggests that they probably derived from a source other than the gut. Their actual function has not been determined.

Most mite-allergic individuals produce antibodies to both the group I and group II allergens.

| Allergen | Mol. Weight | pH |
| --- | --- | --- |
| Group 1 | | |
| Der p I | 24,000 | 4.6–7.4 |
| Der f I | 24,000 | 4.6–7.4 |
| Group II | | |
| Der p II | 15,000 | 5.0–6.4 |
| Der f II | 15,000 | 7.8–8.3 |

Acute exposure to mite allergens has been shown to induce wheezing, rhinitis, eustachian tube obstruction or eczema in sensitized patients. Chronic exposure can cause bronchial hyper-reactivity and chronic asthma. There is a correlation between the level of exposure to house dust mite allergen in early childhood and the likelihood of the subsequent development of asthma. Conversely, asthmatics sensitive to dust mites improve in environments without mites, such as at high altitudes or in hospital rooms. Attempts have therefore been made to decrease patients' exposure to dust mites in the home.

Studies of dust avoidance measures in homes have shown that the use of impermeable mattress and pillow encasings and the removal of bedroom carpeting are associated with a decrease in mite counts. These measures have also been shown to be of clinical value, with a decrease in symptoms and medication requirements occurring in children and adults with dust-sensitive asthma when pillows and mattresses are encased and carpets are removed.

Although carpets and upholstered furniture are major sites of dust mite growth, many allergic individuals are unable or unwilling to remove these from their home. Ordinary vacuuming does not remove dust mites or significantly decrease dust mite allergen levels, and in fact, vacuuming of carpets with the usual household appliances actually increases the amount of airborne dust. However, the use of special filters such as HEPA (High Efficiency Particulate Air) filters or two-ply vacuum bags, and/or the employment of central vacuuming systems (where the dust is collected in a receptacle remote from the room being cleaned) have been helpful. Nevertheless, vacuuming seldom removes all of the live mites, mainly because the mites have little suction cups on the tops of their legs which cause them to cling to textile fibres.

Various chemical agents have been used against mites, including: compounds known under the common names as resuethrin, phenothrin, permethrin, allethrins, tetramethrin, furamethrin, cypermethiin, decamethrin, phenvalerate, phenpropathrin, terallethrin, empenthrin and pyrethrin; pyrethroid compounds such as 1-ethynyl-2-methyl-2-pentenyl-2,2-dimethyl-3,3-(2,2-dichlorovinyl)-cyclopropane-1-carboxylate, 1-ethynyl-2-methyl-2-pentenyl-2,2,3,3-tetramethylcyclopropane-1-carboxylate, α-cyano-3-phenoxybenzyl-2,2-dimethyl-3-(2,2,3-tribromomethyl)-cyclopropane-1-carboxylate; organic phosphorus compounds such as sumithion, fenthion, tetrachlorvinphos, diazinon and DDVP; and carbamate compounds such as those sold under the trademarks Baygon and Sevin. However, these conventional miticides are expensive and are often either toxic to human beings or have the potential themselves to cause allergic or other adverse reactions. Therefore, the use of such compounds in a household environment cannot be the solution to controlling the population of dust mites.

A number of less toxic miticidal agents have been proposed for use in controlling dust mites. As noted in U.S. Pat. No. 4,800,196, these include phenyl salicylate, diphenylamine, methyl beta-naphthyl ketone, coumarin, phenethyl benzoate, benzyl salicylate, phenyl benzoate, N-fluorodichloromethylthio-cyclohexene-dicarboxyimide, p-nitrobenzoic acid methyl ester, p-chlorometaxylenol, α-bromocinnamic aldehyde, 2,5-dichloro-4-bromophenol, 2-phenylphenol, sodium 2-phenylphenolate, 5-chloro-2-methyl-4-isothiazoline-3-one, 2-methyl-4-isothiazoline-3-one and benzimidazolylmethylcarbamate. These can be used in the form of solutions, wettable powders, granules, sprays, etc.

While many of these compounds have some degree of effectiveness against dust mites, their use is not without attendant shortcomings. For example, many of them are rather expensive to produce and/or may be difficult to form into compositions for ordinary domestic use. Elimination of dust in a household environment is a task which is intensely disliked to the point where the average householder is no longer embarrassed by a moderate layer of dust or the presence of "dust bunnies" under beds or behind furniture. Furthermore, as noted above, dust removal and/or vacuuming often stirs up the dust mites and their attendant allergens and, temporarily at least, causes more distress to allergic persons.

More effective methods of reducing exposure to dust mites and their faecal matter, have been developed which do not depend on the diligence of the householder in removing dust.

U.S. Pat. No. 5,271,947 features the use of finely divided sodium chloride powder as a method for killing mites and controlling their allergen-bearing faeces. The powder has the consistency of talcum powder and is used, for example, by applying the powder with a broom or brush to carpets and other textile materials. However, one of the disadvantages in using sodium chloride powder is its hygroscopicity; if the amount used is not carefully controlled, the salt will absorb moisture from the air, particularly in humid climates.

One of the more effective agents for killing dust mites is benzyl benzoate, a compound which is readily available and inexpensive. Powder formulations containing benzyl benzoate are commercially available for application to carpets. British Patent No. 1,368,657 teaches the use of a composition for treating bedding and similar materials which comprises benzyl benzoate and polyethylene glycol, or an ether or ester thereof, as an evaporation retarding agent. British Patent No. 2,042,893 teaches the use of a composition comprising benzyl benzoate and a fatty acid ester for application to bedding and also for treating the skin. A similar composition for general miticidal use in households is taught in published Japanese Patent Application No. 61-91103.

More generally, Bischoff U.S. Pat. No. 4,666,940 teaches the use of various miticidal agents, including particularly benzyl benzoate, as a component in cleansing compositions. The disclosed compositions can also contain dissolved or dispersed plastic materials, but said materials must form discrete particles of particular size and must not form a film.

European Patent Application No. 0,612,469 discloses laundry detergents comprising benzyl benzoate, which compositions are taught to be effective in killing the dust mites present on the articles to be laundered.

In an article by G. Schober et al., "Control of House-Dust Mites (Pyroglyphidae) with Home Disinfectants", *Experimental & Applied Acarology* 3:179–89 (1987), the authors provide data showing that the addition of benzyl benzoate to certain commercially available carpet cleaning formulations results in a composition with better acaricidal properties than other known acaricides.

U.S. Pat. No. 5,180,586 discloses that certain compounds, previously known for use as perfuming agents in foods and cosmetics, have been found to be effective in killing dust mites.

To summarize the published literature, it is apparent that benzyl benzoate and other miticidal compounds disclosed in the art can, under proper conditions of use, be effective in killing dust mites and thus helpful in reducing the level of allergens produced by said mites. Laundering and dry cleaning of textiles and fabrics can also be effective under certain conditions, but this is not practical for day-to-day control.

The principal problem associated with previous methods for controlling dust mites and their allergens is the fact that frequently the mites and their faecal particles are not completely removed. At best, compositions containing acaricidally effective compounds will kill off the mites, but will not remove their faecal matter and the associated allergens. Vacuuming, either by itself or as a final step in a method involving chemical treatment, is often not effective because the pick-up nozzle of the vacuum cleaner cannot effectively fit into all of the crevices in upholstered furniture. Furthermore, unless vacuuming is done under special conditions such as use of a two-ply vacuum bag or HEPA filter, the allergens will be dispersed into the ambient air, therefore doing more harm than good. Therefore, it would be desirable to have a method for controlling dust mites and their associated allergens which would avoid the various disadvantages of the methods heretofore used.

Accordingly, it is a principal object of this invention to provide improved methods for controlling dust particles, in particular, dust mites and the allergens present in their faecal excretions.

It is a further object of this invention to prevent the allergens present in dust and, in particular, dust mites, from entering into the ambient air of indoor spaces.

Another object of this invention is to provide compositions which can be used in attaining the aforementioned objects.

SUMMARY OF THE INVENTION

This invention provides alcohol-based aerosol spray compositions which additionally contain from about 1.0% to about 20.0% of a polymer which is soluble in said alcohol and which, on evaporation, leaves on a sprayed surface a film which acts as a barrier to dust, dust mites and their faecal excretions. (All percentages throughout this disclosure are to be understood as percentages by weight.) The compositions typically also contain water in an amount ranging from 0 to 59%. Alternatively, the polymer can be one which is water-soluble, or one which is soluble in both water and the alcohol; it is preferred that the polymer be soluble in at least the alcohol. In addition, the compositions optionally can include from about 0.1% to, about 10% of an acaricidal ingredient such as benzyl benzoate. Said compositions, in addition to their usual disinfecting properties, are effective aids for controlling dust mites and, when the compositions also contain an acaricidal ingredient, also kill the mites. The compositions can also comprise one or more additional disinfectants such as a quaternary ammonium compound, a phenol-based antimicrobial agent, or a botanical oil with disinfectant properties. The compositions can also comprise a suitable propellant, and other ingredients such as wetting agents, surfactants, preservatives and anti-corrosion agents.

The mites and allergens associated with dust mites can be controlled by applying, more particularly by spraying, the compositions of this invention onto the surface of textile fabrics infested with said mites. This sets up a barrier which prevents the dust mites and their excreted faecal matter from coming in contact with people. In addition, in the embodiment of this invention where the composition additionally includes an acaricidal ingredient such as benzyl benzoate, the mites are killed and the production of additional allergens thereby halted.

The method according to this invention comprises, in its broadest sense, spraying onto a textile fabric surface an alcohol-based disinfecting composition which contains from about 1.0% to about 20.0% of a polymer soluble in said alcohol and which, on evaporation, leaves on the surface a film which acts as a barrier to dust mites and their faecal excretions and to other particles present in household dust and their associated allergens. The compositions typically also comprise water and, alternatively, the polymer can be one which is water-soluble. The compositions optionally can include from about 0.1% to about 10% of an acaricidal ingredient such as benzyl benzoate, in which case the method is additionally a method for killing dust mites. In many circumstances, particularly with the infestation of dust mites is not great, this spraying step will provide effective control of dust mite allergens by preventing their escape into the ambient air.

A more effective method for control of dust particles, in particular dust mites and their associated faecal matter, is to remove as many dust mites and faecal particles as possible by vacuuming under conditions where the particles are not blown into the ambient air; for example, using a two-ply filter system or an HEPA system. The vacuuming step is then followed up by spraying the fabric surface with a composition described above.

A still further procedure for dust mite control involves a three-step method, the first step being application to the fabric surface, for example, by spraying of a composition comprising a known acaricidal agent, such as benzyl benzoate. This is followed up, after a suitable time for drying, by vacuuming as discussed above. In this procedure, the vacuuming step is somewhat more effective since most of the mites are dead and not clinging to the fibres. The final step is spraying the fabric surface with an aerosol composition according to this invention.

DETAILED DISCLOSURE

The aerosol compositions of this invention comprise, as essential ingredients, an alcohol having from 1 to 4 carbon atoms, preferably ethanol, and a polymer soluble in the alcohol, which results in a barrier film on a surface when the alcohol evaporates. The compositions will typically and preferably also comprise up to about 15% of water and, as an alternative, the polymer can be one which is soluble in water. However, the use of an alcohol-soluble polymer is preferable in view of the faster evaporation rate of alcohol.

The compositions can also include an acaricidal ingredient such as benzyl benzoate or another known chemical substance effective against dust mites such as those disclosed in U.S. Pat. No. 4,800,196, pertinent portions of which are incorporated herein by reference.

In view of the fact that dust mites are invisible to the naked eye, it is logical, from a commercial point of view, to control dust mites simultaneously with killing or controlling other invisible organisms such as bacteria. Aerosol disinfectant compositions have attained wide consumer acceptance and the addition of one or more ingredients which will control dust mites and/or remove the dust mite allergens from ambient air has an extremely beneficial purpose and there is no need to persuade potential consumers to purchase an additional household care product specifically for the purpose of dust mite control.

As contemplated by this invention, the principal disinfecting ingredient is a low molecular weight alcohol, typically an alcohol having from 1–4 carbon atoms such as methanol, ethanol or isopropanol, with ethanol being preferred. The disinfecting properties of such alcohols are well known. They form the basis of many commercial disinfecting compositions and such compositions have attained great consumer acceptance. In addition to its disinfecting properties, the alcohol also functions as a solvent for the polymer and for some of the other ingredients optionally present in the compositions of this invention and provides for rapid drying time in a household environment.

The amount of alcohol present in the composition ranges from about 30% to 90%, preferably from 70% to 85%, based on the weight of the composition, and exclusive of any propellant contained in said composition.

Water, if present in the composition, can comprise up to about 59% of said composition. Preferably, any water present will be in the 5 to 15% range.

The polymer used in the compositions of this invention is preferably one which is soluble in the alcohol component and must be a polymer which, after spraying and evaporation of the solvents in the composition, will leave a protective barrier film on the sprayed surface. Obviously, any such polymer must meet the criteria of consumer safety and, since the contemplated use of the compositions is in an indoor environment, the polymer should not have an offensive odor. All polymers which meet the foregoing criteria are suitable for inclusion in the subject compositions and these include, but are not limited to, polyester resins, acrylate polymers and copolymers, methacrylate polymers and copolymers, polyvinyl pyrrolidone and copolymers comprising vinyl pyrrolidone, butyl maleate/isobornyl acrylate copolymers, thermoplastic polyamides, nylon resins, polyvinyl alcohols and polyether polyols. A suitable group of ethanol-soluble polymers are polyacrylates and their copolymers. Because of their known safety, film-forming polymers used in hair treatment formulations have been found to be especially suitable. Examples include certain of the products sold under the following trade designations: Advantage CP, Gaffix, Gantrez and the PVP/VA Series of International Specialty Products; Amphomer, Versatyl and Resyn of National Starch & Chemical Company; Dantoin of Lonza Inc.; Delsette of Hercules Incorporated; Diaformer of Clariant Corporation; Luviflex, Luviset, Luviquat and Luviscol of BASF Corporation; and Stepanhold of Stepan Company. These polymeric substances are generally soluble in ethanol; some are also soluble in water. The significant feature of the polymer useable in this invention is that it must form a film which will act as a barrier to both dust mites themselves and to their faecal excretions. A powder is not suitable for this purpose, and likewise a polymer film which immediately breaks down to flakes or particles will not be suitable. The film should remain intact for at least seven days, preferably for a period of from 10 to 30 days.

The amount of polymeric material in the composition is from about 1% to about 20% by weight, preferably from 1% to 7%, and more preferably from 2% to 5% by weight, exclusive of any propellent in said composition.

In another embodiment of this invention, the subject compositions additionally contain a miticidal ingredient, such as benzyl benzoate, in an amount of up to about 10% by weight. Preferably, the benzyl benzoate is present in an amount ranging from 0.5% to 8%, and more preferably from 1% to 7%.

The compositions of this invention may also contain one or more additional antimicrobial agents in order to increase the antimicrobial effectiveness of the composition up to a level defined by the United States Environmental Protection Agency as "hospital strength disinfection". The term "hospital strength" is not intended to indicate that the subject compositions are restricted to use in hospitals and other health care facilities; rather such disinfectant compositions are commonly sold for domestic use, and the term simply indicates a higher level of disinfective activity.

Although any known disinfecting agent can be used as an optional additional component, preferably the disinfectant agent will comprise one or more quaternary ammonium compounds commonly used as disinfectants or one or more of the well known phenolic compounds such as ortho-phenylphenol. The additional antimicrobial ingredient may be present in the composition in amounts ranging from about 0.01 weight percent to about 1 weight percent, preferably from 0.05 to 0.5 weight percent, and more preferably about 0.1%, based on total weight of the composition.

If the additional antimicrobial component is a quaternary ammonium salt, any of the broad classes of suitable quaternary ammonium compounds may be used. More than one quaternary ammonium compound is employed to assist in providing a broader spectrum antimicrobial efficacy. Useful quaternary ammonium compounds include, for example, those quaternary ammonium compounds represented by the formula:

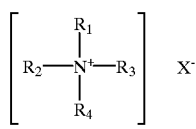

wherein $R_1$, $R_2$, $R_3$, and $R_4$ may be described in three general groups. The counterion X may be any salt-forming anion which permits water solubility of the quaternary ammonium complex. Exemplary counterions include halides, for example chloride, bromide or iodide, or methosulfate.

In a first group of preferred quaternary ammonium compounds, $R_1$ and $R_2$ are $C_1$–$C_7$ alkyl groups (preferably methyl groups); $R_3$ is a benzyl group or a benzyl group substituted with an alkyl group having about 1 to 18 carbon atoms or an alkyl group having about 8 to 20, and preferably 8 to 18, carbon atoms; $R_4$ is a benzyl group or a benzyl group substituted with an alkyl group having about 1 to 18 carbon atoms, and $R_4$ is a benzyl group or a benzyl group substituted with an alkyl group having about 1 to 18 carbon atoms or an alkyl group having about 8 to 20, and preferably 8 to 18 carbon atoms.

In a second group of preferred quaternary compounds, $R_1$, $R_2$ and $R_3$ are $C_1$ to $C_7$ alkyl (preferably methyl groups); and $R_4$ is an alkyl, an alkyl-substituted benzyl, or a phenyl-substituted alkyl group having a total of from about 8 to 20, and preferably 8 to 18, carbon atoms.

In a third group of preferred quaternary ammonium compounds, $R_1$ is an alkyl, an alkyl substituted benzyl, or a phenyl substituted alkyl group having a total of from about 10 to 20, and preferably from 12 to 16 carbon atoms; $R_2$ is a $C_1$–$C_7$ alkyl (preferably a methyl group); $R_3$ is $[CH_2CH_2O]_xH$; and $R_4$ $[CH_2CH_2O]_yH$, with the sum of x+y varying between about 2 and 50 (preferably 2 and 5). For all these groups, X may be a halide (preferably chloride or bromide) or may be a suitable organic anion such as benzoate or saccharinate.

Quaternary ammonium compounds are well known and available commercially from a number of suppliers. For example, diallcyl dimethyl ammonium chloride is available in approximately 50% active ingredient solution as Bardac-2050 quaternary ammonium compound from Lonza, Inc. (Fairlawn, N.J.) and Bio-Dac-50-20 quaternary ammonium compounds is available from Bio-Labs (Decatur, Ga.), both of which are mixtures of approximately 25% octadecyl dimethyl ammonium chloride, about 10% dioctyl dimethyl ammonium chloride, about 15% didecyl dimethyl ammonium chloride in a solvent solution containing about 10–20% ethyl alcohol and 30–40% water. Also, for example, alkyl dimethyl benzyl ammonium chloride is available in an approximately 80% active ingredient solution as BTC-8358 from Stepan Co. (Northfield, Ill.); Bio-Quat-80-28RX from Bio Lab, and Barquat-MB80-10 is available from Lonza. The latter two have an alkyl distribution of approximately $C_{14}$ (50%), $C_{12}$ (40%) and $C_{16}$ (10%), and diluents of ethyl alcohol (10%) and water (10%). In addition, a dialkyl dimethylbenzyl ammonium saccharinate in 33% alcohol solution is available from Stepan Company as Onyxide 3300.

If the additional antimicrobial ingredient is a phenolic derivative, any suitable phenol compound may be used. These include phenol, halogenated phenols, phenylphenols particularly ortho-phenylphenol, xylenols, nitrophenols, cursols, thymol, nitrophenols, aminophenols, and many others well known in the art.

The compositions of this invention may also include one or more surfactants in concentration ranging from 0.035 to about 10 weight percent, preferably from 0.04 to 2 weight percent based on the total weight of the composition (excluding the propellant required in aerosol formulations). The surfactants can be cationic, anionic, or nonionic. However, when the compositions contain a quaternary ammonium compound as an additional disinfecting agent, the surfactants present should be limited to nonionic surfactants.

Examples of suitable nonionic surfactants are as follows: ethoxylated fatty alcohols containing from 11 to 15 carbon atoms in the alcohol and from 3 to 40 moles of ethylene oxide (Tergitol nonionics, Union Carbide Corporation), isomeric linear secondary alcohols with 11 to 15 carbon atoms and 9 moles of ethylene oxide (Tergitol 15-S-9), and linear primary alcohols with 12 to 15 carbon atoms and 9 moles of ethylene oxide (Tergitol 25-L-9); the block copolymers of polyoxyethylenepolyoxypropylene ("Tetronic series nonionic surfactants", BASF Wyandotte Corporation); ethylene glycol-reacted polyoxyethylene-polyoxypropylene copolymers of the formula [HO(CH$_2$C—H$_2$O)$_x$(CHCH$_3$—CH$_2$O)$_y$(CH$_2$CH$_2$O)$_z$)$_2$H], such as, for example, where x, y and z respectively are 13, 30 and 13 (Pluronic L-64; BASF Wyandotte Corporation); alkyl phenol ethoxylates such as nonylphenoxypolyethoxyephenol ethoxylates or nonylphenoxypolyethoxyethanol with 9 to 10 moles of ethylene oxide (Triton N-101; Rohm & Haas Co.); alkanolamides for example, fatty acid alkanolamides having one or two hydroxyethyl or hydroxypropyl groups such as coconut and tallow fatty acid ethanolamide and diethanolamide, and oleic acid diethanolamide; and silicone glycol copolymers such as those sold as Dow Corning 190, 193 or 1315.

The compositions of this invention should have a pH in the range of 8 to 11. In order to attain a suitable pH, it is usually necessary to add alkalising agents which include well-known substances such as sodium hydroxide, potassium hydroxide, ammonium hydroxide, mono-, di- and tri-ethanol amines, and other agents well known in the art.

The compositions of the invention may also comprise one or more optional constituents including, but not limited to: pH buffering agents, preservatives, fragrances, fragrance carriers and adjuvants which increase their miscibility in the aqueous compositions, colorants, hydrotropes, antifoaming agents, anti-oxidants and corrosion inhibitors, as well as others known to the art but not particularly elucidated herein.

In a preferred form, the compositions of this invention are supplied in self-contained valve controlled aerosol units which provide a fine spray or foam upon activation of the valve. The aerosol container unit consists of a pressure-tight aerosol container having a valve control opening and containing the composition of this invention and from about 2 to about 10% of a propellant. Propellants are selected from the well known compatible propellants such as carbon dioxide, isobutane, n-butane, n-propane and mixtures thereof The propellant used should not adversely react with any components of the composition.

In the methods according to this invention, the subject compositions are sprayed onto textile surfaces such as sofas, upholstered chairs, bedding, pillows, rugs, carpets, etc. known to be infested with dust mites. Although in describing all of these methods, emphasis is placed on dust mites and their allergens, it should be understood that these methods are equally effective against dust particles in general and against other allergens associated therewith, including pollen and animal dander. The preferred mode of application is by means of a self-contained aerosol spraying device. Spraying should be carefully done, ensuring that, for example, all sides of pillows are sprayed, that the spray reaches to corners and crevices, etc. The spraying step alone will reduce the amount of allergens by preventing the escape of dust mite faecal particles into the ambient atmosphere.

A more effective method of dust mite control involves an initial step of vacuuming up from textile surfaces as many as possible of the dust mites and their associated faecal particles. It is important, when performing this step, that the vacuuming be done under conditions whereby the particles are not blown into the ambient air. A central vacuum system, where a holding bag is remote from the area being cleaned, will fulfill this purpose. However, since this is not practical in most households, an acceptable alternative is to use a vacuum system which has a high performance filter, such HEPA filters, or to employ a two-ply vacuum bag. Immediately after the vacuuming step, the compositions of this invention should be sprayed onto the textile surfaces according to the method described above. It is particularly advantageous to apply the compositions immediately after vacuuming since the vacuuming step will have removed most of the dust particles, thereby permitting the film formed by the composition to make closer contact with the fabric surface. Additionally, if the composition contains an acaricidal ingredient, such as benzyl benzoate, the composition will also kill off the mites which have not been removed in the vacuuming step.

An even more effective method of dust mite control includes, as a preliminary first step, the application of a composition comprising an acaricidally effective ingredient such as, for example, benzyl benzoate. These compositions, which are most conveniently applied in aerosol form, should be sprayed onto the fabric surface, permitted to dry, and then vacuumed up with a vacuuming system of the type described in the foregoing paragraph.

In this method, which is recommended for severe mite infestations, the dust mites are killed, and the dead mites and their faecal particles are removed. This should be followed up immediately by spraying onto the surface a composition according to this invention. If the composition includes an acaricidal ingredient, such as benzyl benzoate, in addition to the film forming polymer, any mites which survived the onslaught of the first two steps of the process, are likely to be killed.

The invention will be better understood by reference to the following examples, which are included for purposes of illustration only.

EXAMPLE 1

A liquid composition was prepared which had the following ingredients in the percentage indicated:

| Ingredient | wt. % |
| --- | --- |
| Anhydrous ethanol[1] | 82.741 |
| Amphomer LV-71[2] | 3.646 |
| Aminomethylpropanol (AMP) 95[3] | 0.750 |
| Onyxide 3300 (33%)[4] | 0.334 |
| Corrosion inhibitors | 0.500 |
| Fragrance | 0.052 |
| DI Water | 11.977 |

[1]SDA 40-2; USI Chemical
[2]Amphoteric acrylic polymer; National Starch & Chemical Co.
[3]Angus Chemical Company
[4]Quarternary antimicrobial surfactant; Stepan Company Into a clean dry mixing vessel containing the ethanol, Amphomer LV-71 was slowly added under agitation until the polymer dissolved. AMP 95 was then added and mixed until uniform. The remaining ingredients were added in the order indicated above. The pH was measured and shown to be in the range of 9.0 to 10.6.

An aerosol formulation was then prepared which contained 96% by weight of the above-described liquid composition and 4% of carbon dioxide. The pressure range was 95 to 105 psi.

EXAMPLE 2

A liquid formulation was prepared which had the following constituents in the percentages indicated.

| Ingredient | wt. % |
| --- | --- |
| Anhydrous ethanol | 82.741 |
| Benzyl Benzoate[5] | 4.792 |
| Onyxide 3300 (33%) | 0.334 |
| Amphomer LV-71 | 3.646 |
| Aminomethylpropanol (AMP) 95 | 0.750 |
| Corrosion inhibitors | 0.500 |
| Fragrance | 0.052 |
| DI Water | 7.185 |

[5]Kalama Chemical Co.

The method of preparation was identical to that of Example 1 with the additional ingredient, benzyl benzoate, being added concurrently with the Onyxide 3300. A clear colorless solution was obtained having a pH range of from 9.0% to 10.6%.

An aerosol formulation was then prepared which contained 96% by weight of the above-described liquid and 4% of carbon dioxide.

The formulations of Examples 1 and 2 were tested on fabric samples and the results showed reduction in the numbers of dust mites and in the amount of dust particles.

EXAMPLES 3–7

Using the general methods of Examples 1 and 2, additional liquid compositions were prepared having the following ingredients in the percentage indicated. In preparing these compositions, the ammonium hydroxide was the last ingredient added and was added in sufficient amount to provide a pH within the desired range.

| | Weight % | | | | |
| --- | --- | --- | --- | --- | --- |
| Ingredient | Ex. 3 | Ex. 4 | Ex. 5 | Ex. 6 | Ex. 7 |
| Anhydrous ethanol | 82.741 | 82.741 | 82.741 | 89.662 | 82.745 |
| Amphomer LV-71 | 5.208 | | | | 5.208 |
| Advantage Plus[6] | | 5.208 | | | |
| PVP K-30[7] | | | 5.208 | | |
| Dermacryl 79[8] | | | | 3.954 | |
| Benzyl Benzoate | | | | 4.792 | |
| Aminomethyl propanol | 0.911 | 0.911 | 0.911 | | 0.911 |
| Ammonyx DMCD-40[9] | 0.200 | 0.200 | 0.200 | 0.200 | 0.200 |
| Triethanolamine (99%) | | 0.200 | 0.200 | 0.200 | 0.200 |
| Onyxide 3300 | | | | 0.334 | |
| FC-138[10] | | 1.000 | 1.000 | | |
| Forestall[11] | | | | | 0.061 |
| Ammonium Hydroxide (26 baume) | 0.100 | 0.100 | 0.100 | 0.650 | 0.100 |
| Silwet 7002[12] | | | | 0.208 | |
| DI Water | 10.640 | 9.640 | 9.640 | | 10.574 |

[6]copolymer of vinyl acetate, butyl maleate and isobornyl acrylate in ethanol
[7]polyvinylpyrrolidone
[8]acrylate copolymer comprising octylacrylates, butylacrylates and methacrylate
[9]lauryldimethylamine oxide (40%)
[10]fluorosurfactant: flurochemical salt in isopropanol and 2-butoxy ethano
[11]N-soya-N-ethylmorpholinium ethosulphate
[12]polyalkyleneoxide modified polydimethylsiloxane Aerosol formulations were prepared from all of the foregoing compositions which contained 96% by weight of said liquid compositions and 4% of carbon dioxide.

While described in terms of the currently preferred embodiments, it is to be understood that the present disclosure is to be interpreted as by way of illustration, and not by way of limitation, and that various modifications and alterations apparent to one skilled in the art may be made without departing from the scope and spirit of the invention.

We claim:

1. A method for controlling dust mites and their allergens present in textile surfaces which comprises the steps of
   (1) vacuuming up from said surfaces, under conditions whereby particles present on said surfaces are not vented into the ambient surroundings, the dust mites and their faecal particles, and
   (2) spraying onto said surfaces an aerosol composition comprising: from 90% to 98% of a composition which comprises from 30% to 90% of a $C_1$–$C_4$ alcohol, from 0% to 59% of water, an effective amount of benzyl benzoate as an acaricidal agent, and from 1% to 20% of a polymer soluble in said alcohol which, upon evaporation of the alcohol and water, leaves a film on said surface; and from 2% to 10% of a propellant.

2. A method according to claim 1 in which, in the composition, the alcohol is ethanol.

3. A method according to claim 2 in which the composition comprises from 1% to 7% of the polymer.

4. A method according to claim 3 in which the composition comprises from 70% to 85% ethanol and from 2% to 5% of the polymer.

5. A method according to claim 1 in which, in the composition, the polymer is an acrylate polymer or copolymer.

6. A method according to claim 1 in which, in the composition, the benzyl benzoate is present in an amount of from 0.1% to about 10.0% by weight.

7. A method according to claim 1 in which the composition additionally comprises one or more antimicrobial ingredients.

8. A method according to claim 7 in which an antimicrobial ingredient is a quaternary ammonium salt.

9. A method according to claim 1 in which the composition comprises from 0% to 15% water.

10. A method for controlling dust mites and their allergens present in textile surfaces which comprises the steps of
    (1) spraying on to said surfaces a first aerosol composition comprising: from 90% to 98% of a composition which comprises an effective amount of benzyl benzoate as an acaricidal agent; and from 2% to 10% of a propellant,
    (2) permitting said first composition to dry on said surfaces,
    (3) vacuuming up from said surfaces, under conditions whereby particles present on said surfaces are not vented into the ambient surroundings, the dust mites and their faecal particles, and
    (4) spraying onto said surfaces a second aerosol composition comprising: from 90% to 98% of a composition which comprises from 30% to 90% of a $C_1$–$C_4$ alcohol, from 0% to 59% of water and from 1% to 20% of a polymer soluble in said alcohol which, upon evaporation of the alcohol and water, leaves a film on said surface; and from 2% to 10% of a propellant.

11. A method according to claim 10 in which the benzyl benzoate in the first composition is present in an amount of from 0.1% to about 10.0% by weight.

12. A method according to claim 10 in which, in the second composition, the alcohol is ethanol.

13. A method according to claim 12 in which the second composition comprises from 1% to 7% of a polymer.

14. A method according to claim 13 in which the second composition comprises from 70% to 85% ethanol and from 2% to 5% of the polymer.

15. A method according to claim 10 in which the polymer in the second composition is an acrylate polymer or copolymer.

16. A method according to claim 10 in which the second composition additionally comprises one or more antimicrobial ingredients.

17. A method according to claim 10 in which an antimicrobial ingredient is a quaternary ammonium salt.

18. A method according to claim 10 in which the second composition comprises from 0% to 15% water.

* * * * *

UNITED STATES PATENT AND TRADEMARK OFFICE
CERTIFICATE OF CORRECTION

PATENT NO. : 6,428,801 B1
DATED : August 6, 2002
INVENTOR(S) : Janette Suh, Laura Vaccaro and Robert William Bogart It is certified that error appears in the above-identified patent and that said Letters Patent is hereby corrected as shown below:

Title page,
Add Item:
-- Related U.S. Application Data,

[63] Division of Application No.09/126,193 filed July 30, 1998, now U.S. Patent No. 6,117,440. --

Column 14,
Line 1, change "10" to -- 16 --.

Signed and Sealed this

Twelfth Day of October, 2004

JON W. DUDAS
*Director of the United States Patent and Trademark Office*